（12）United States Patent
Ormsby et al.

(10) Patent No.: US 8,934,989 B2
(45) Date of Patent: Jan. 13, 2015

(54) RADIO FREQUENCY BASED ABLATION SYSTEM AND METHOD WITH DIELECTRIC TRANSFORMER

(75) Inventors: Theodore C. Ormsby, Escondido, CA (US); Russell Chung, San Diego, CA (US); George Leung, San Diego, CA (US); Gwo Jenn Shen, Carlsbad, CA (US)

(73) Assignee: MedWaves, Inc., San Diego, CA (US)

( * ) Notice: Subject to any disclaimer, the term of this patent is extended or adjusted under 35 U.S.C. 154(b) by 396 days.

(21) Appl. No.: 12/424,287

(22) Filed: Apr. 15, 2009

(65) Prior Publication Data

US 2010/0268219 A1 Oct. 21, 2010

(51) Int. Cl.
*A61F 2/00* (2006.01)
*A61B 18/18* (2006.01)

(52) U.S. Cl.
CPC .............. *A61B 18/18* (2013.01); *A61B 18/1815* (2013.01); *A61B 2018/1853* (2013.01); *A61B 2018/1869* (2013.01)
USPC ............................................ 607/101; 606/41

(58) Field of Classification Search
USPC .............. 606/32, 33, 41, 48, 49, 50; 607/101, 607/102, 154, 156
See application file for complete search history.

(56) References Cited

U.S. PATENT DOCUMENTS

| | | | |
|---|---|---|---|
| 5,275,597 A | 1/1994 | Higgins et al. | |
| 5,957,969 A | 9/1999 | Warner et al. | |
| 6,190,382 B1 | 2/2001 | Ormsby | |
| 6,663,625 B1 | 12/2003 | Ormsby et al. | |
| 6,706,040 B2 | 3/2004 | Mahon et al. | |
| 7,070,595 B2 | 7/2006 | Ormsby et al. | |
| 2003/0078573 A1 | 4/2003 | Truckai et al. | |
| 2006/0287649 A1 | 12/2006 | Ormsby et al. | |
| 2006/0293650 A1* | 12/2006 | Prakash et al. | 606/33 |
| 2006/0293651 A1* | 12/2006 | Cronin | 606/33 |
| 2007/0066972 A1 | 3/2007 | Ormsby et al. | |
| 2007/0233057 A1* | 10/2007 | Konishi | 606/33 |
| 2008/0015570 A1 | 1/2008 | Ormsby et al. | |
| 2008/0033424 A1 | 2/2008 | Van Der Weide | |
| 2009/0082762 A1 | 3/2009 | Ormsby et al. | |

FOREIGN PATENT DOCUMENTS

| | | |
|---|---|---|
| EP | 2008604 | 12/2008 |
| WO | WO-2006/084676 A1 | 8/2006 |
| WO | 2007135437 | 11/2007 |

OTHER PUBLICATIONS

"About". Macmillan Dictionary. <http://www.macmillandictionary.com/dictionary/american/about>.*

(Continued)

*Primary Examiner* — Kami A Bosworth
(74) *Attorney, Agent, or Firm* — Casari and McKenna, LLP

(57) ABSTRACT

An ablation device which transmits radio frequency (RF) energy for the ablation of biological tissues has elongate inner and outer coaxial conductors extending from a proximal portion to a distal portion. An RF antenna is disposed at the distal portion of the device and transmits RF energy for ablation of a tissue region to be treated. Reflection of energy from the tissue or the ablation point is reduced by providing multiple layers of dielectric media about the antenna, or by providing a gradual transition point from the conductors to the antenna tip, by means of a longitudinally stepped dielectric layer transformer.

26 Claims, 6 Drawing Sheets

(56) References Cited

OTHER PUBLICATIONS

"Similar". Macmillan Dictionary. <http://www.macmillandictionary.com/dictionary/american/similar>.*

Notification, International Search Report and Written Opinion dated Nov. 30, 2010 for PCT/US10/31266.

R.W.P. King et al., Insulated Linear Antenna—Theory and Experiment, Journal of Applied Physics, vol. 46, No. 3, pp. 1091-1098, Mar. 1975.

* cited by examiner

RADIO FREQUENCY BASED ABLATION SYSTEM AND METHOD WITH DIELECTRIC TRANSFORMER

BACKGROUND

1. Field of the Invention

The present invention concerns a radio frequency (RF) based system for ablating tissue and occlusions, particularly within liquid-filled lumens of animals, such as the heart, liver, arteries and vessels of a human, with an electrical field produced about an RF antenna, and is particularly concerned with reducing reflected signal losses in such a system.

2. Related Art

Therapeutic tissue ablation systems apply energy to a biological ablation tissue site via different energy exchange means, such as heat conduction and irradiation. These systems may employ various energy modes, such as radiofrequency, ultrasound, laser, cryogenic, and the like. Within the radio frequency (RF) range, certain microwave ablation systems are used to destroy or ablate biological tissues. In one application, a microwave ablation system is used to ablate cardiac tissues that cause irregular heartbeats or arrhythmia, avoiding the need for more risky and invasive open heart surgery. In such an application, an ablation member such as an RF antenna is incorporated as part of a catheter or probe. The catheter is passed through the vein for access to the atrium. Within the atrium, the RF antenna is positioned at the desired location where ablation is applied.

Microwave ablation systems can also be used in treatment of other biological sites such as arteries, organs and body vessels. As an example, a microwave ablation system is used to ablate tumors in the lungs, liver, kidney or other areas of the body.

These surgical and therapeutic applications require an efficient system for the transmission of radio frequency energy to the ablating member for the delivery of energy to the target tissue site. U.S. Patent Application Publication No. 20080015570 of Ormsby et al. describes a tissue ablation system comprising a hollow conductive coaxial cable having a first inner elongated electrically conductive tubular member having a distal end portion, the first tubular member having a hollow, axially extending lumen, a second elongated electrically conductive member disposed in a substantially coaxial relationship over at least a portion of the first electrically conductive tubular member over substantially the length of the cable, a dielectric medium disposed between the first and second electrically conductive tubular members, and an ablating member or radio-frequency antenna which delivers radio frequency energy including microwaves to body tissue disposed at the distal end portion of the cable. The radio-frequency antenna is adapted to receive and irradiate radio-frequency energy in the microwave range at a frequency typically greater than 300 Megahertz (MHz) in the electromagnetic spectrum for ablating biological tissue along a biological ablation pathway.

Typical microwave tissue ablation systems have a RF power supply which provides RF energy along the coaxial cable or waveguide to the antenna. Most current tissue ablation systems are designed to provide a set impedance, which may be of the order of 50 ohms. However, the impedance on the catheter side of the system tends to vary, for example due to coaxial cable characteristics and variations in the electromagnetic properties of the tissue under treatment. It is known that the dielectric constants of different types of tissue, for example heart tissue and liver tissue, are different. Also, the dielectric properties of the tissue change as the tissue is treated. This prevents a fixed electromagnetic RF supply circuit from achieving maximum performance in delivering the highest amount of RF energy to the tissue being treated. In U.S. Pat. No. 6,190,382 of Ormsby, a microstrip transformer between the RF energy source and the transmission line or catheter is used to adapt the 50 ohm system more closely to the ablation antenna impedance.

In U.S. Pat. No. 7,070,595 of Ormsby et al., a tissue ablation system and method is described in which the output frequency of the RF energy pulses supplied to the catheter is adjusted to effect a substantial match with the RF antenna and biological tissue load impedance. In this system, a bi-directional coupler samples the forward pulses supplied to the microwave transmission line or co-axial cable and the reflected pulses which are reflected from the target ablation tissue, and uses the signal samples as feedback to a controller which varies the frequency in order to reduce the reflected signal, so that more energy is applied to the tissue undergoing ablation. U.S. Pat. No. 5,957,969 of Warner et al. describes a mechanically tuned microwave ablation catheter system and method which has a tuner located in the power supply, the transmission line, or the antenna which changes the antenna configuration, moves material relative to the antenna, or alters the waveguide.

SUMMARY

The present invention provides an improved radio frequency based system for ablating biological tissues of a body vessel, including the atrium of a patient, in which the RF frequency coupling at the antenna-tissue interface is increased by appropriate modification of the antenna design, by use of a dielectric transformer or gradient between the active antenna area and the tissue interface, by providing a transition area between the coaxial cable and the antenna tip, or by utilization of both techniques.

In one embodiment, a device for transmitting radio-frequency energy for the ablation of biological tissue comprises an outer elongated electrically conductive tubular member having an axial lumen; an inner elongated electrically conductive member disposed in a substantially spaced apart relationship within the lumen of the outer tubular member and extending beyond the distal end of the outer tubular member to define a wave guide configured for the transmission of radio-frequency energy in the microwave frequency range and above; and an antenna adapted to receive and radiate the radio frequency energy for the ablation of biological tissues which is electrically coupled to the inner member and distally spaced from the distal end of the outer tubular member to leave an air gap. In one embodiment, the inner electrically conductive member is a tubular member which extends coaxially within the lumen of the outer tubular member.

This arrangement creates a space or transition area between the emitting arm of the antenna and the return arm or outer tubular member of the device, providing an intentional discontinuity. This reduces the dependence of the system on tissue parameters, by providing a single-ended driver circuit.

In another embodiment, a multi-layer dielectric transformer or dielectric stack is provided in the distal end portion of the device. The dielectric transformer may comprise at least two dielectric layers of different materials arranged in a dielectric stack on the outer surface of the antenna which are designed to provide a gradual transition or dielectric gradient between the surface of the antenna and the surrounding lossy medium or tissue interface. The dielectric layers may comprise alternating layers of high and low dielectric constant thin film arranged to reflect any tissue reflected signals back into the tissue. The layers may have a thickness equivalent to ¼ of the wavelength of interest.

In yet another embodiment, a tissue ablation device is provided in which a gradual transition point is provided from the coaxial cable of the device and the antenna tip, by means of a plurality of dielectric layers which terminate at longitudinally spaced location from the cable to the tip of the device. This gradual transition mitigates the mode conversion loss due to the change from the tranverse electromagnetic mode (TEM) mode of propagation in the coaxial cable to the mode pattern of the electromagnetic field propagating in the tissue, reducing localized heating effects which can occur with abrupt transitions.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for a radio frequency energy transmission device, which incorporates a wave guide for conducting radio frequency (RF) energy, particularly microwave energy, for the ablation of biological tissues. The wave guide has an outer tubular conductor and an inner conductor within the lumen of the outer conductor which extends up to a distal portion of the device. An ablating member such as a radio frequency (RF) antenna which delivers radio frequency energy, particularly microwave energy, is located at the distal portion of the wave guide. Various arrangements are provided for improving coupling of energy into the tissue to be treated are provided in the different embodiments, including a dielectric stack around the antenna, a spacer or discontinuity in one of the cables connected to the antenna, and a longitudinal dielectric transformer to provide a gradual transition point from the coaxial cable to the transformer.

After reading this description, it will become apparent to one skilled in the art how to implement the invention in various alternative embodiments and alternative applications. However, although various embodiments of the present invention will be described herein, it is understood that these embodiments are presented by way of example only and not limitation. As such, this detailed description of various alternative embodiments should not be construed to limit the scope or breadth of the present invention as set forth in the appended claims.

Figure 1:
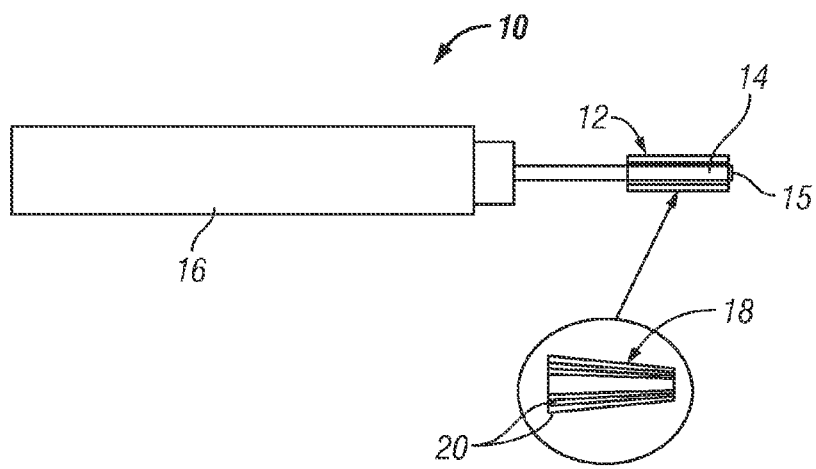
FIG. 1 is a schematic diagram of an ablation device according to one embodiment with multiple dielectric layers around the antenna.

FIG. 1 illustrates a first embodiment of a radio frequency (RF) wave guide device or probe 10 forming part of a microwave ablation system. The microwave ablation system is similar to that described in U.S. Pat. App. Pub. Nos. 20080015570 and 20090082762 of Ormsby et al., the contents of both of which are incorporated herein by reference. Device 10 is generally tubular and has a multi-layer construction with a central bore or guidewire lumen extending along its length from a proximal portion (not illustrated) to distal portion 12. A radio frequency (RF) ablation antenna 14 is located at the distal end portion of the device. Inner and outer electrically conductive tubular members or coaxial conductors extend coaxially from the proximal portion of the apparatus, with at least the inner conductor extending up to a location close to the distal end or tip 15 of the antenna. The inner conductor may be non-tubular in alternative embodiments. An RF transmission wave guide is defined between the inner and outer conductors. An outer jacket or casing 16 of dielectric polymer material encloses the co-axial conductors along at least a major portion of the length of the device 10.

The inner and outer conductors each comprise an elongated electrically conductive tubular member, with the outer conductor arranged in a substantially coaxial relationship over at least a portion of length of the inner conductor. This arrangement defines an annular space between the walls of the inner and outer conductors where a dielectric medium is placed. The dielectric medium may be a solid or a fluid or a combination of solid and fluid which fills the space between the inner and outer conductor. Any unfilled space may be evacuated to form a vacuum or filled with an alternative dielectric solid or fluid material. A dielectric fluid medium such as air may be dispensed in lieu of a solid dielectric layer. Vacuum, which also exhibits dielectric property, may be introduced by the evacuation of air and sealing the space between the distal and proximal end portions of the cable during manufacture. Alternately, a vacuum source may be configured in fluid communication with the space between the inner and outer conductors.

Figure 2:
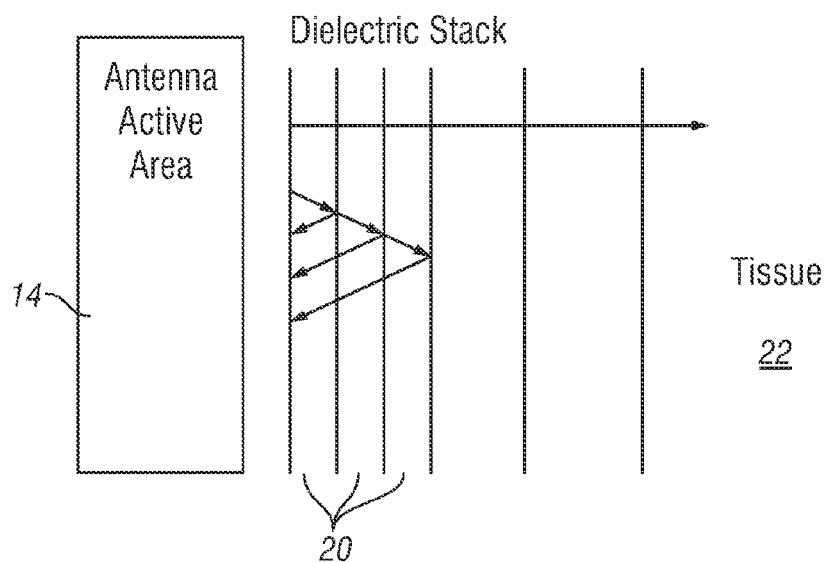
FIG. 2 is a representative diagram showing the concept of providing a dielectric gradient between the metal and tissue interface with the device of FIG. 1.

In this embodiment, the ablation antenna 14 located at the distal portion 10 of the apparatus may be a monopole or dipole antenna or a helical coil antenna, which is electrically coupled to at least the inner conductor of the coaxial cable device. The antenna is adapted to receive and radiate electromagnetic energy from a source of radio frequency energy coupled with the inner and outer coaxial conductors. In alternative embodiments, other forms of ablation devices or radio frequency antennas may be used in place of the antenna 14, such as a pair of spaced electrically conductive microstrips disposed at the distal end portion of the coaxial cable device, as described in U.S. Pat. No. 6,663,625, the contents of which are incorporated herein by reference. In prior art antenna arrangements, the ablation antenna is coated with a single layer of dielectric encapsulant material. The abrupt interface between antenna and the tissue interface prevents electromagnetic energy from effectively coupling into tissue. Typically, the electric field experiences a reflection at the interface between the insulation layer and the external medium, in this case tissue. This results in high reflection loss being experienced at the amplifier output port. Without a proper management scheme, this can lead to damage to a high output microwave amplifier. In the embodiment of FIG. 1, a dielectric stack 18 of two or more layers 20 of different dielectric materials surrounds the active area of the antenna so as to produce a dielectric gradient between the active antenna area 14 and the surrounding tissue 22 to be treated, as indicated in FIG. 2.

It is well known art in the area of optics that by depositing multiple layers of alternating high and low dielectric constant thin film, (especially with a certain thickness equivalent to the ¼ wavelength of the wavelength/frequency of interest), the energy transmission and reflection characteristics may be altered. The embodiment of FIG. 2 takes advantage of the destructive and constructive interference of these ¼ wavelength stacks (to the incident electromagnetic waves) to improve transmission into the tissue. With a properly optimized dielectric layers, the efficiency of the ablation antenna may be improved and optimized. As illustrated in FIG. 2, some of the energy is reflected back at the transition between the dielectric layers, but a larger amount of overall energy is transmitted into the tissue 22 than would be transmitted with only a single dielectric layer or coating. Various parameters of the dielectric layers 20 may be varied in order to achieve the desired transmission level, for example the thickness, refractive index, and the like. In one embodiment, the dielectric layers are arranged to produce a dielectric gradient which reduces or minimizes reflection of electromagnetic energy at the tissue/antenna interface. One or more of the layers may be air.

In one embodiment, a single layer of dielectric medium having a dielectric constant less than the dielectric constant of the antenna material or insulator material surrounding the antenna may be provided over the antenna tip. This layer has a thickness equal to ¼ of the wavelength of the RF signal. This produces reflections which interfere destructively with each other. A single layer can eliminate reflections at one wavelength. A multi-layer coating as illustrated in FIGS. 1 and 2 can reduce losses over a broader electromagnetic spectrum. Thus, a second layer of a dielectric medium may be provided over the first layer, with the second dielectric medium having a higher dielectric constant than the first in order to further reduce losses over a broader electromagnetic spectrum. Additional layers may be provided with alternating higher and lower dielectric constants and different thicknesses in order to further adjust and reduce losses, and dielectric stacks may be designed for specific applications as needed. The dielectric media may be any suitable solid or fluid media, including air, with a suitable containment structure for fluid media.

Utilizing multiple layers of dielectric media, the energy coupling of the antenna tip can be improved. Although the example illustrated in FIG. 1 illustrates the use of a tubular dielectric sheet to implement the dielectric stack, a deposition method which deposits two or more layers of dielectric, anti-reflection coatings may be used in alternative embodiments to create the desirable dielectric gradient. As shown in FIGS. 1 and 2, the dielectric layer provides a gradual transition from the surface of the antenna to the surrounding lossy medium, reducing the risk of the wave propagation along the ablation tip being shorted out prematurely.

Some examples of suitable dielectric materials for the dielectric layers include Fluoropolymers: PTFE (polytetrafluoroethylene), Dielectric-Constant (DC) range of 2.1 to 2.3, FEP (Fluorinated Ethylene Propylene), DC range of 2.1 to 2.4, PEEK (Polyetheretherketones), DC range of 3 to 3.6, Ceramic DC range of 3 to 100 plus, Polyethylene, DC range of 2.1 to 2.3. These can be applied in coatings or tubular sheaths. Air, DC range of 1 to 1.1, can be also mixed with many of materials above to produce hybrid dielectric values, and vacuum may also be incorporated in the dielectric stack.

Figure 3:
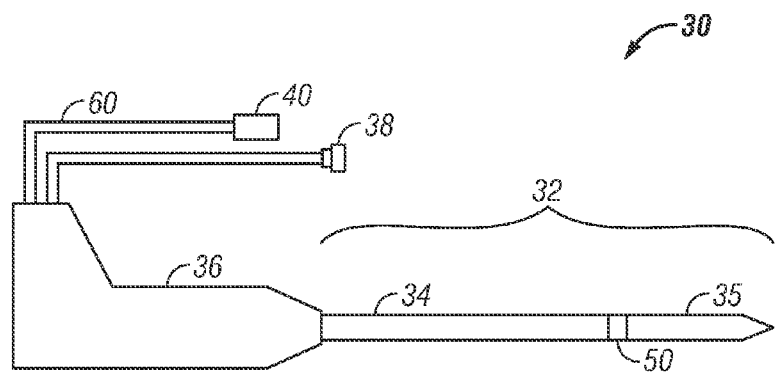
FIG. 3 is a representative diagram of a tissue ablation system according to a second embodiment including a coaxial cable ablation device with a spacer.
Figure 4:
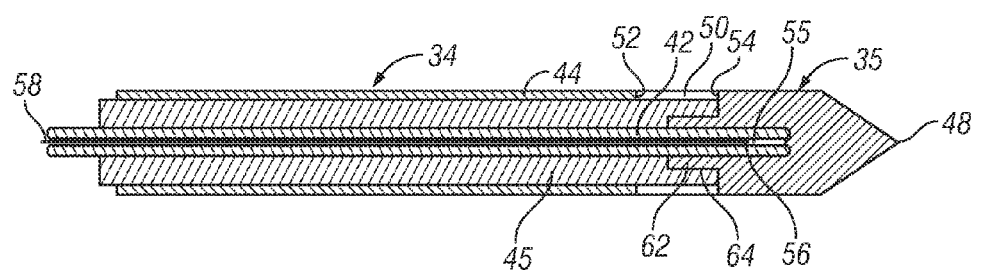
FIG. 4 is an enlarged cross-sectional view of the coaxial cable ablation device of the system of FIG. 3.

FIG. 3 is a schematic diagram of a tissue ablation system 30 according to another embodiment, while FIG. 4 is a cross sectional view of at least part of the coaxial cable device 32 of the system having a coaxial cable waveguide 34 and an antenna 35 at the distal end of device 32. A handle 36 is connected to the proximal end of the waveguide 34. An RF signal generator 38 is connected through the handle to the waveguide 34. Output signals from the waveguide are connected through the handle to a signal processor 40, for example as described in U.S. Pat. No. 7,594,913, the contents of which are incorporated herein by reference.

In this embodiment, the coaxial cable waveguide 34 has an inner tubular conductor 42 and an outer tubular conductor 44 coaxial with the inner conductor, with a layer 45 of dielectric material between the conductors. In the illustrated embodiment, antenna 35 is a monopole antenna with a pointed end 48, and is secured to the distal end of the waveguide with a spacer or air gap 50 between the distal end 52 of outer conductor 44 and the opposing end face 54 of the antenna. The inner conductor 42 has a distal end portion which projects into the antenna, and has a central hollow lumen 55 in which a temperature sensor 56 is located, in this case in the portion of the conductor which extends into the antenna, although it may be located elsewhere in other embodiments. The temperature sensor wires 58 extend from the sensor through the lumen 55 and through the handle to connect to signal cable 60. The inner end face of the antenna 35 has a central projecting boss 62 which surrounds inner conductor 42 and extends into a corresponding cylindrical cavity or end bore 64 in the distal end of dielectric layer 45, providing a more secure junction between the waveguide and antenna. An outer shield layer (not illustrated) extends over the outer conductor 44, and the outer surface of the antenna is also coated with at least one protective layer of dielectric material (not illustrated). In one embodiment, an outer dielectric layer extends over the outer conductor, air gap, and at least part of the antenna so as to provide mechanical support. The antenna tip may have a coating layer of a different dielectric material.

The arrangement of FIGS. 3 and 4 provides an air gap which produces a transition area or discontinuity between the emitting arm of the antenna and the return arm or return current side of the electromagnetic structure. The air gap provides more control of the transition between the positive and negative poles of the antenna, thus avoiding or reducing the abrupt transition from the coaxial cable to the antenna which can lead to localized heating of the surrounding tissue.

Figure 5:
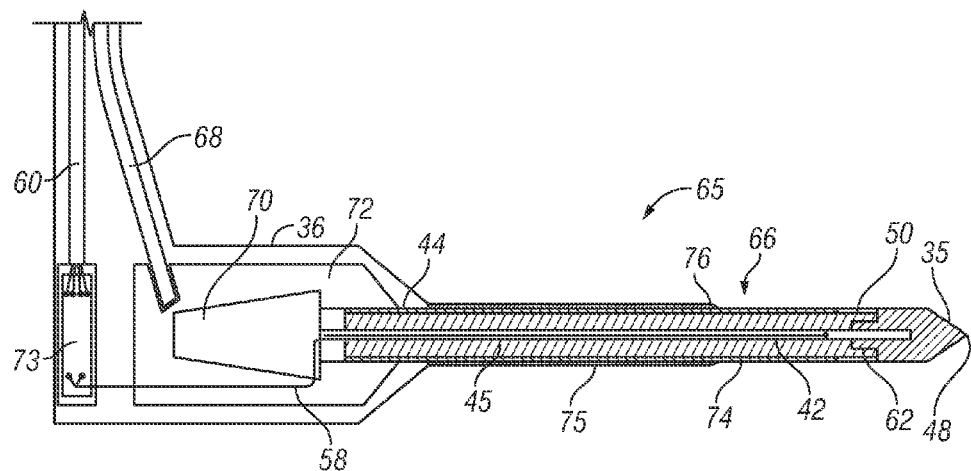
FIG. 5 is a cross-sectional view of a third embodiment of a tissue ablation system with a coaxial cable ablation device having a longitudinal dielectric transformer.

FIG. 5 illustrates another embodiment of an RF ablation system 65 in which the coaxial cable device 66 is similar to that of FIG. 4 but includes additional dielectric layers. The system 65 is otherwise identical to that of FIG. 4 and like reference numbers are used for like parts as appropriate. In FIG. 5, the handle 36 is cut away to reveal the inner control circuitry in more detail. As illustrated in FIG. 5, the RF signal cable 68 is connected to a transformer circuit 70 on a printed circuit board 72. Transformer circuit 70 is designed to adapt the normal 50 ohm impedance of the microwave system more closely to the ablation antenna impedance, as described, for example, in U.S. Pat. No. 6,190,382 of Ormsby, the contents of which are incorporated herein by reference. A temperature detection circuit 73 is also located on a PCB within the handle and connects the temperature sensor wires 58 to signal cable 60.

As noted above, the coaxial cable device 66 of FIG. 5 is similar to that of FIG. 4, and includes a waveguide having inner and outer coaxial conductors 42, 44 with a dielectric layer 45 between the conductors, and an antenna 35 secured to the distal end of the waveguide, with an air gap 50 between the distal end of outer conductor 42 and the opposing end face of antenna 35. In this embodiment, two outer layers 74,75 of different dielectric materials are provided on the outside of the outer conductor 44, with the first outer layer 74 extending beyond the distal end of conductor 44 and over part of the outer surface of antenna 35, terminating short of the tip of the antenna. The second outer dielectric layer 75 terminates at point 76, short of the distal end of the outer conductor 44. This arrangement provides a gradual transition from the ablation coaxial cable to the antenna tip, i.e. a longitudinally stepped transition from the end of outer dielectric layer 75, to the end of the outer conductor 44, to the air gap 50, and to the end of the first dielectric layer 74. In this embodiment, the tip of the antenna is also coated with dielectric material.

The embodiment of FIG. 5 provides a gradual transition point from the ablation coaxial cable to the antenna tip, reducing reflection from the tissue or the ablation point. The coaxial cable naturally supports a TEM mode due to its symmetric design. However, at the antenna ablation point, the distribution of the electromagnetic field in the tissue cannot be a TEM mode of the coaxial cable due to its open boundary nature and the different dielectric properties. As a result, a mode conversion loss occurs, which is a well known problem with coaxial cable ablation devices. One method to mitigate this conversion loss is to gradually transition from the TEM mode to the mode pattern of the tissue, and this can be done either with a dielectric stack around the antenna producing a gradual transition, as shown in FIG. 1, or with a longitudinal dielectric transformer with longitudinally stepped dielectric layers, as in FIG. 5.

Figure 6:
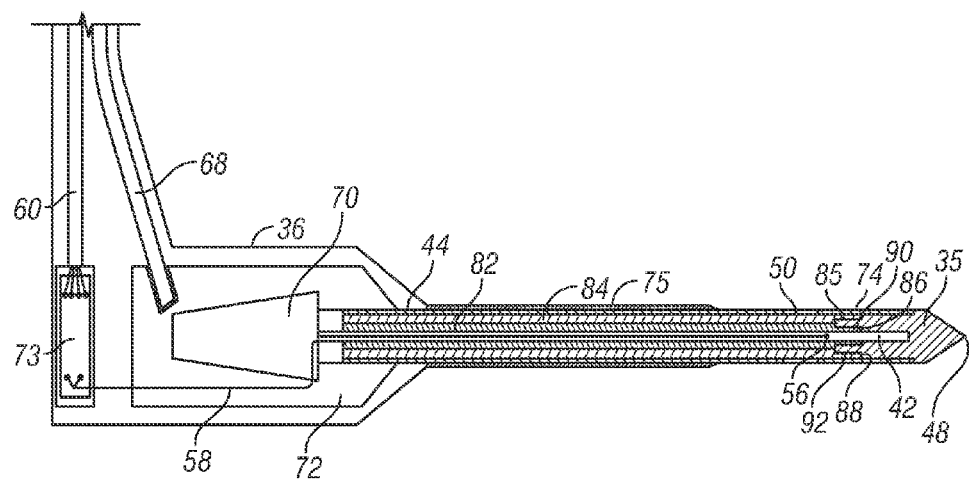
FIG. 6 is a cross-sectional view of another embodiment of a coaxial cable ablation device having a modified dielectric transformer and spacer arrangement.

FIG. 6 illustrates another embodiment of a coaxial cable device 80, which is similar to the previous embodiment, except for a modification of the inner dielectric material and the mating ends of the inner dielectric and the inner end of the antenna. Since the embodiment of FIG. 6 is otherwise identical to that of FIG. 5, like reference numbers are used for like parts as appropriate. In this embodiment, the inner dielectric layer of FIG. 5 is replaced with two concentric, tubular layers 82, 84 of different dielectric materials. Another difference is that the outer tubular conductor extends over the outer surface of the antenna 35 to a location close to the distal tip of the antenna, with the first outer dielectric layer 74 extending over the distal end of the outer conductor. In this embodiment, the annular air gap or discontinuity 50 is provided in the length of the outer conductor at a location spaced rearward of the antenna 35. The opposing end faces of the antenna and inner dielectric layers are also modified in this embodiment. Instead of a central projecting boss 62 at the inner end of the antenna, the antenna has a projecting boss 85 with a central annular indent 86 and concentric outer indent 88, while the opposing end faces of the two dielectric layers 82, 84 have a mating structure of a central boss 90 projecting into indent 86 and an outer, annular projecting rim 92 in layer 84 which extends into outer indent 88. This adds further mechanical strength to the connection between the coaxial cable and antenna.

Figure 7:
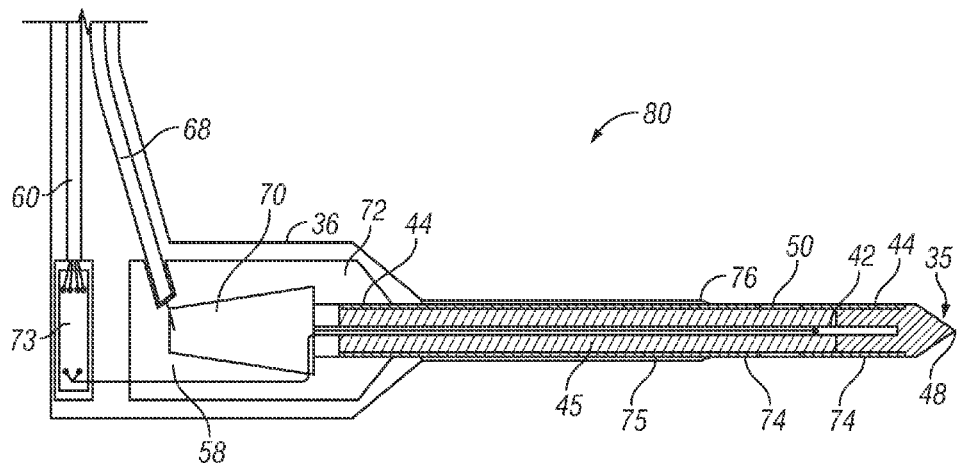
FIG. 7 is a cross-sectional view of another embodiment of a coaxial cable ablation device having a modified dielectric transformer and spacer arrangement.

FIG. 7 illustrates another coaxial cable device 80 which is a modification of the embodiments of FIGS. 5 and 6. In this embodiment, the outer conductor 44 and outer dielectric layers 74, 75 are similar to the previous embodiment. A single inner dielectric layer 45 is provided, and the opposing end faces of the dielectric layer 45 and antenna 35 are flat. The opposing faces may be suitably bonded together with adhesive or the like in this embodiment and the previous embodiments.

Figure 8:
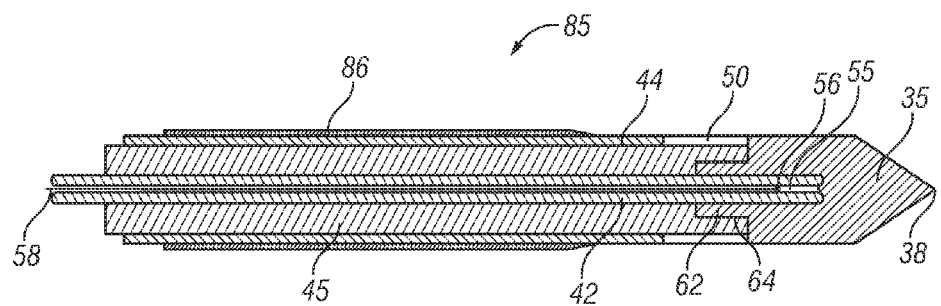
FIG. 8 is a cross-sectional view of another embodiment of a coaxial cable ablation device which is similar to the embodiment of FIG. 4 but adds another dielectric layer.

FIG. 8 illustrates another coaxial cable device 85 which is a modification of the embodiment of FIG. 4, and like reference numbers have been used for like parts as appropriate. Device 85 is identical to the device 32, apart from the addition of an outer waveguide insulation layer 86 of dielectric material which terminates prior to the distal end of conductor 44. The inner conductor 42, dielectric 45, outer conductor 44, and outer dielectric layer 86 are in a coaxial arrangement.

Figure 9:
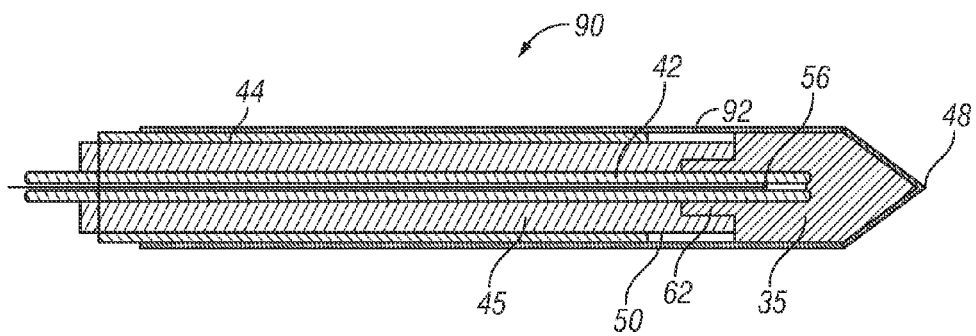
FIG. 9 is a cross-sectional view of another embodiment of a coaxial cable ablation device in which the additional dielectric layer is extended over the spacer and antenna tip.

Another embodiment of a coaxial cable device 90 is illustrated in FIG. 9. This embodiment is similar to that of FIG. 8, except that the outer dielectric layer 92 in this embodiment extends over the waveguide spacer or air gap 50 and over the antenna up to the antenna tip 48. One or more outer layers of dielectric material may be provided in this embodiment. Again, the dielectric inner and outer layers and the inner and outer conductors are in a coaxial arrangement.

Figure 10:
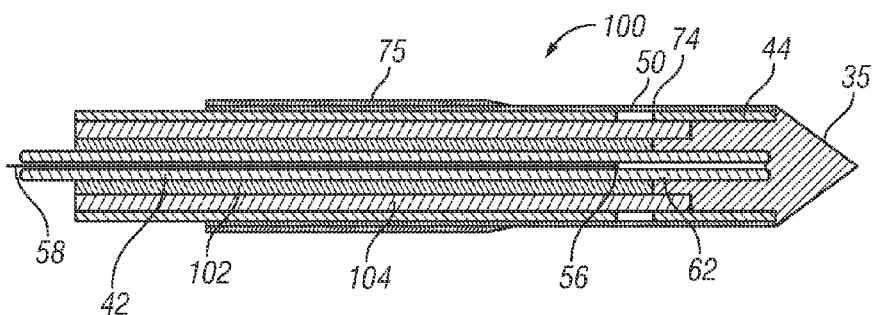
FIG. 10 is a cross-sectional view of another embodiment of a coaxial cable ablation device with multiple dielectric layers.

FIG. 10 illustrates another embodiment of a coaxial cable device 100 with another different possible antenna and waveguide design. This embodiment is similar in some respects to the embodiment of FIG. 7, and like reference numerals have been used as appropriate. As is the case with FIG. 7, the waveguide in this embodiment has inner and outer coaxial conductors 42, 44, and two inner layers of different dielectric materials 102, 104 between the conductors. As is the case with the embodiment of FIG. 7, the outer conductor 44 extends over part of the outer surface of antenna 35, and the annular space or air gap 50 is provided in the outer conductor at a location spaced rearward of the antenna. Also as in FIG. 7, two outer layers 74, 75 of different dielectric materials are provided, one of which extends up to the distal end of outer conductor 44, with the outermost layer 75 terminating rear of the air gap 50. The main difference between FIGS. 7 and 10 is the interface or connection between the inner dielectric layers 102, 104 and the inner end of the antenna 35. In this case, the innermost inner dielectric layer 102 terminates short of the distal end of the outermost of the inner dielectric layers 104, defining a central indent, and a central boss 62 is provided on the inner face of the antenna (similar to FIG. 9) and extends into mating central indent of the dielectric layers.

Figure 11:
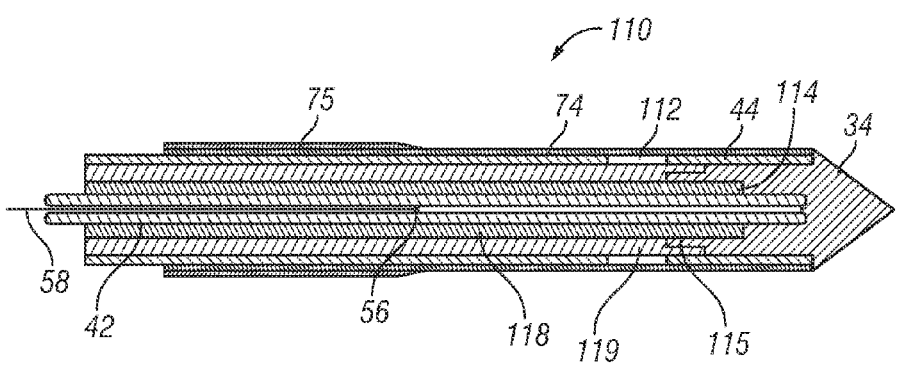
FIG. 11 is a cross-sectional view of another embodiment of a coaxial cable ablation device with a modified antenna design and multiple dielectric layers.

FIG. 11 illustrates another modified embodiment of a coaxial cable device 110 which is similar to that of FIG. 10, except for the interface between the waveguide and antenna, the position of temperature sensor 56, and the length of the air gap or spacer 112, and like reference numbers are used for like parts as appropriate. As in the previous embodiment, this embodiment has a waveguide which comprises coaxial inner and outer tubular conductors 42, 44, with the outer tubular conductor 44 extending over at least part of the outer surface of antenna 35. As in the previous embodiment, first and second outer layers 74 and 75 are provided around the outer conductor 44, with the first outer layer 74 extending up to the distal end of conductor 44, and the second outer layer terminating at a location rear of the spacer 112, which is longer than the air gap or spacer 50 in the previous embodiment. As in the previous embodiment, two inner layers 118, 119 of different dielectric materials are provided, but unlike the previous embodiment, the innermost of the dielectric layers is longer than the outermost of the inner dielectric layers, and extends into a central bore or indent 114 in the inner end face of the antenna 35. Also, the outermost layer has an indent into which an annular projecting rib 115 of the antenna 35 extends. In this embodiment, the position of the temperature sensor 56 in the central bore or lumen 55 of inner conductor 42 is different from the previous embodiments, and is located rearward of the previous embodiment. Thus, in some cases, the temperature sensor is located in the region of antenna 35, while in others it is spaced to the rear of the antenna in the vicinity of the air gap or spacer, and in others it is spaced rearward of the air gap or spacer.

Figure 12:
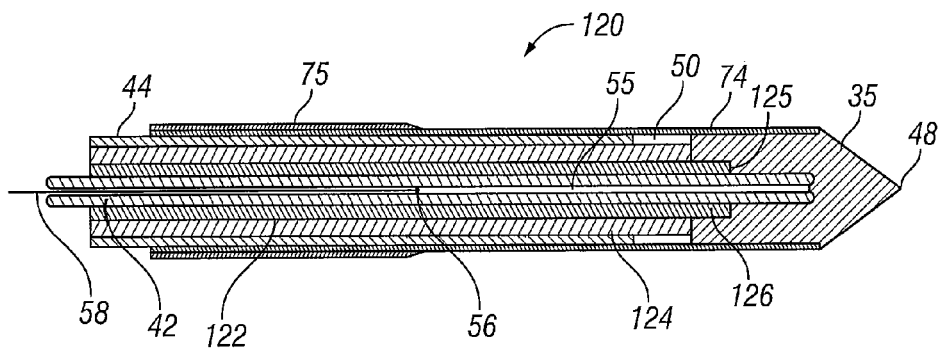
FIG. 12 is a cross-sectional view of another embodiment of a coaxial cable ablation device.

FIG. 12 illustrates another embodiment of a coaxial cable device 120 which is similar to the embodiment of FIG. 5 except that the single inner dielectric layer 45 is replaced with two concentric dielectric layers 122, 124, the shape of the interface or connection between the antenna and waveguide is modified, and the position of the temperature sensor 56 is changed. The device 120 is otherwise identical to that of FIG. 5, and like reference numbers are used as appropriate. The shape of the inner end face of antenna 35 is modified, and has a central cylindrical indent 125 instead of a projecting boss. The innermost dielectric layer 122 has a distal end portion 126 extending beyond the distal end of the surrounding dielectric layer 124 and into the central indent 125 of antenna 35. This helps to align and secure the antenna to the distal end of the waveguide. The temperature sensor is positioned rear of the interface between the antenna and waveguide, at approximately the same axial location as the distal end of the outer dielectric layer 75.

Figure 13:
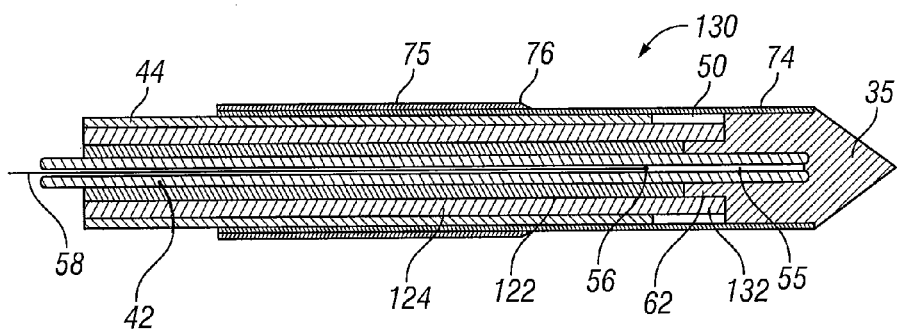
FIG. 13 is a cross-sectional view of another embodiment of a coaxial cable ablation device with a modified antenna and dielectric layer design.

FIG. 13 illustrates a modified coaxial cable device 130 according to another embodiment which is similar to the embodiment of FIG. 12, except that the interface between the waveguide and antenna and the shape of the inner end of the antenna are modified. In this case, the antenna end face has a central projecting boss 62, as in FIG. 5, and the outermost layer 124 of the two inner dielectric layers has a distal end portion 132 extending beyond the distal end of the innermost layer 122 and surrounding boss 62. The position of the temperature sensor 56 is also spaced forward from the position in FIG. 12. The embodiments of FIGS. 12 and 13 show some other possible antenna and waveguide designs.

Figure 14:
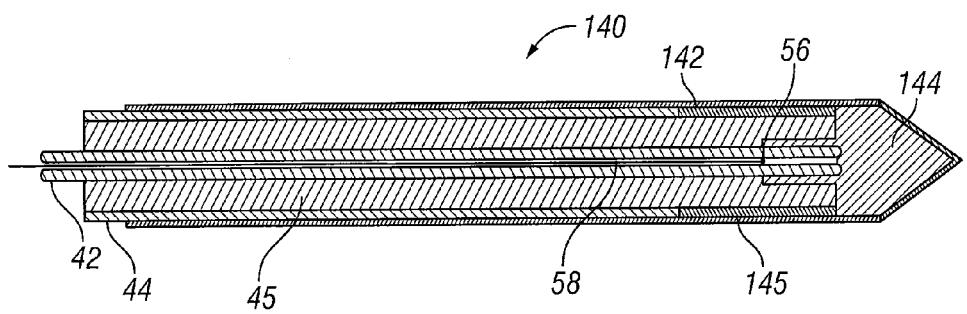
FIG. 14 is a cross-sectional view of another embodiment of a coaxial cable ablation device having both a helical coil antenna and a monopole antenna tip.

FIG. 14 illustrates another modified coaxial cable device 140 according to another embodiment. This embodiment has both a helical antenna 142 and a monopole antenna tip 144 at the distal end portion of the coaxial cable device. As in previous embodiments, device 140 has inner and outer coaxial conductors 42, 44 with a dielectric layer 45 (or multiple dielectric layers) between the conductors. The outer conductor terminates short of the monopole antenna tip 144, and the helical coil antenna 142 extends between the distal end of outer conductor 44 and the antenna tip 144. The distal end portion of inner conductor 42 protrudes into the antenna tip 144 in a similar manner to previous embodiments, and inner conductor 42 has a hollow lumen 55. Temperature sensor 56 is located in a distal end portion of lumen 55 adjacent the proximal end of the monopole antenna tip 144, and temperature sensor wires 58 extend through the lumen and handle of the device to connect to a signal cable. An outer insulation or dielectric layer 145 covers the entire waveguide and antenna up to the tip of monopole antenna 144 in the illustrated embodiment. Alternatively, the layer 145 may terminate short of the tip, or multiple layers of different dielectric materials may be provided as in previous embodiments in order to create and control the RF field.

In FIG. 14, opposite ends of the helical antenna may be connected to the distal end of the outer conductor 44 and to the inner conductor via the distal antenna tip 144. Alternatively, the helical antenna may have an end which is open, i.e. not connected to an inner or outer conductor. For example, a gap may be provided between the distal end of the helical antenna 142 and the antenna tip 144, or between the proximal end of helical antenna 142 and the distal end of outer conductor 144, so that only one end is connected to a conductor. Alternatively, both ends of the helical antenna are open, i.e. neither end is connected to a conductor, and the helical antenna floats between the outer conductor and the tip. Each of these alternatives provides different antenna turning capabilities for matching with different biological tissue impedances.

The embodiments of FIGS. 4 to 14 show some of the many possible antenna designs utilizing one or more layers of dielectric material between the inner and outer conductors, as well as different antenna body and tip shapes, different spacer lengths, and zero to multiple layers of outer insulation materials. These different designs can be used to create and control the RF field about the antenna. In each of these embodiments, a dielectric stack may also be provided around the antenna, as described above in connection with FIGS. 1 and 2, in order to reduce reflection of energy and transmit a larger amount of the RF energy into the tissue.

In the foregoing embodiments, the inner and outer tubular members may be of any suitable conductive material, and may be flexible when incorporated in a steerable device or may be rigid when incorporated in a rigid probe device. One or both conductive tubular members may be of electrically conductive wire mesh or braided material, or electrically conductive thin film material. The monopole antenna may have a pointed tip as in the illustrated embodiments, or may have a rounded, atraumatic tip in alternative embodiments.

Antenna design is one of the most important aspects of an ablation system since it is the final delivery point of the RF power. Some important factors are to make the antenna small enough for ease of use and also so as to be minimally invasive, while also designing it to be an efficient radiator. The dielectric constant of the tissue helps on the size reduction but it also makes the antenna very dependent on its surroundings. In the embodiments described above, a quasi-dipole design is adopted by modifying a ground plane-less mono-pole to act as a dipole. This provides a single ended driver circuit and the ability to reduce or minimize to some extent the dependence on the tissue parameters. For example, since the dipole is totally immerged within the tissue dielectric, the resonance frequency is also dependent on the tissue parameters. The quasi-dipole approach makes it easier to accommodate this variation without sacrificing the ablation results. The designs of the coaxial cable assembly in the foregoing embodiments provide better matching of the antenna to the surrounding tissue properties for increased RF energy coupling into the tissue, by reducing abrupt interfaces between the coaxial cable device and tissue in various ways, for example by incorporating an air gap in the electrical path from one conductor to the antenna, by providing a dielectric stack about the antenna which provides a dielectric gradient and reduces reflections, and/or by providing a longitudinally stepped dielectric transformer of plural layers of dielectric which terminate at stepped intervals along the device.

Furthermore, to minimize or reduce the interaction of the tissue characteristic and the probe resonance frequency, the interfacial material on the exterior of the probe is selected to allow efficient radiation and yet reduce the dependence of the device on the tissue parameters. The probe radiation efficiency may be further improved if the coaxial cable devices described above are coupled with an RF frequency adjustable ablation system, as described, for example, in U.S. Pat. No. 7,070,595 of Ormsby et al., the contents of which are incorporated herein by reference. A smaller cable diameter footprint may also be achieved by utilizing a microstrip circuit.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are, therefore, representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A device for transmitting radio-frequency energy for the ablation of biological tissue comprising:
   an outer elongated electrically conductive tubular member having an axial lumen, a distal end, and a proximal end;
   an inner elongated electrically conductive tubular member disposed in a spaced apart relationship within the lumen of the outer tubular member to define a wave guide configured for the transmission of radio-frequency (RF) energy in the microwave frequency range and above, the inner member having a distal end and a proximal end;
   an antenna electrically coupled to at least the distal end of the inner member and adapted to receive and radiate the RF energy for the ablation of biological tissues, the antenna having an outer surface; and
   at least two layers of dielectric medium arranged in a stack circumferentially around the outer surface of the antenna and configured to provide a dielectric gradient in a direction extending radially outward from the antenna between the antenna and the surrounding tissue in order to reduce reflection from the tissue, the layers being of different dielectric media which have different dielectric constants.

2. The device according to claim 1, wherein the antenna is a monopole.

3. The device according to claim 1, further comprising a dielectric medium between the inner member and the outer tubular member.

4. The device according to claim 3, wherein the dielectric medium has an internal recess at its distal portion to receive at least a portion of the antenna.

5. The device according to claim 3, wherein the antenna has an internal recess which receives a distal portion of the dielectric medium.

6. The device according to claim 1, further comprising a dielectric ring member between the antenna and the outer tubular member.

7. The device according to claim 1, wherein radio frequency energy is the microwave frequency range of approximately 300 MHz and up.

8. The device according to claim 1, wherein at least one of the electrically conductive tubular members is formed of an electrically conductive wire mesh.

9. The device according to claim 1, wherein at least one of the electrically conductive tubular members is formed of an electrically conductive braided material.

10. The device according to claim 1, wherein at least one of the electrically conductive tubular members is formed of an electrically conductive thin-film material.

11. The device according to claim 1, wherein the antenna has a pointed distal tip.

12. The device according to claim 1, wherein the antenna has an atraumatic distal tip.

13. The device according to claim 1, wherein the inner and outer electrically conductive members comprises flexible materials.

14. The device according to claim 1, wherein the distal end portion of the inner member extends beyond the distal end of the outer tubular member.

15. The device according to claim 1, wherein the layers of dielectric media around the antenna have a thickness approximately equal to one quarter of the wavelength of the RF energy, the first layer having a dielectric constant less than that of the distal end portion of the device and the second layer having a dielectric constant greater than that of the first layer.

16. The device according to claim 1, wherein the inner conductive member comprises a tubular member extending coaxially with the outer layer.

17. A device for transmitting radio-frequency energy for the ablation of biological tissue comprising:
   an outer elongated electrically conductive tubular member having an axial lumen and an outer surface;
   an inner elongated electrically conductive member disposed in a spaced apart relationship within the lumen of the outer tubular member to define a wave guide configured for the transmission of radio-frequency energy in the microwave frequency range and above;
   at least a first antenna electrically coupled to at least the inner member and adapted to receive and radiate the radio frequency energy for the ablation of biological tissues, the antenna having an outer surface and a distal end;
   the outer tubular member having a distal end portion having a distal end which is distally spaced from the antenna to define a gap in the path from the outer tubular member to the antenna, the gap comprising an air gap; and
   at least a first outer layer of dielectric material extending circumferentially around the outer surface of the outer tubular member along at least the distal end portion of the outer tubular member, the first outer layer having a distal portion extending distally from the distal end of the outer tubular member and over the gap up to the first antenna, and not projecting beyond the distal end of the antenna.

18. The device of claim 17, wherein the first antenna comprises a monopole having a distal tip defining a distal end of the device.

19. The device of claim 17, further comprising a dielectric medium between the inner member and the outer tubular member.

20. The device of claim 19, wherein the dielectric medium extends beyond the distal end of the outer tubular member up to the antenna.

21. The device of claim 20, wherein the dielectric medium has an internal recess at its distal end which receives at least a portion of the antenna.

22. The device of claim 21, wherein the distal end portion of the inner member protrudes into the antenna.

23. The device of claim 20, wherein the antenna has an internal recess at its proximal end which receives a distal portion of the dielectric medium.

24. The device of claim 23, wherein the distal portion of the inner member protrudes beyond the distal portion of the dielectric medium into the antenna.

25. The device of claim 17, wherein the inner conductive member comprises a tubular member which is disposed in a coaxial relationship within the lumen of the outer tubular member.

26. The device of claim 17, further comprising a second outer layer of dielectric material extending over at least part of the length of the first outer layer, the first and second layers being of different dielectric materials.

* * * * *